United States Patent [19]
Arbogast et al.

[11] Patent Number: 5,133,777
[45] Date of Patent: Jul. 28, 1992

[54] ADJUSTABLE LOWER LIMB PROSTHESIS AND APPARATUS AND METHOD FOR THE ADJUSTMENT THEREOF

[75] Inventors: Joseph Arbogast; Robert Arbogast, both of Mount Sterling, Ohio

[73] Assignee: Ohio Willow Wood Company, Mount Sterling, Ohio

[21] Appl. No.: 512,260

[22] Filed: Apr. 20, 1990

[51] Int. Cl.⁵ .................................................. A61F 2/62
[52] U.S. Cl. ....................................... 623/38; 623/27; 623/901; 264/DIG. 30
[58] Field of Search ............... 623/38, 27, 24, 901; 606/78; 264/DIG. 30

[56] References Cited

U.S. PATENT DOCUMENTS

| | | |
|---|---|---|
| 2,485,827 | 10/1949 | Hartzell . |
| 2,684,487 | 7/1954 | Hansen et al. . |
| 3,400,408 | 9/1968 | Garcia . |
| 3,659,294 | 5/1972 | Glabiszewski . |
| 4,149,280 | 4/1979 | Wilson . |
| 4,215,441 | 8/1980 | Wilson . |
| 4,221,007 | 9/1980 | Wilson .................................. 623/38 |
| 4,314,398 | 2/1982 | Pattersson . |
| 4,397,048 | 8/1983 | Brown et al. . |
| 4,473,421 | 9/1984 | Gustafsson ......................... 623/28 X |
| 4,523,338 | 6/1985 | May . |
| 4,547,913 | 10/1985 | Phillips . |
| 4,564,365 | 1/1986 | Winer et al. . |
| 4,704,129 | 11/1987 | Massey ................................... 623/25 |
| 4,822,363 | 4/1989 | Phillips ................................... 623/27 |
| 4,938,776 | 7/1990 | Masinfer ................................. 623/49 |

FOREIGN PATENT DOCUMENTS

| | | | |
|---|---|---|---|
| 1291855 | 4/1969 | Fed. Rep. of Germany | 623/27 |
| 2101254 | 7/1972 | Fed. Rep. of Germany | 623/38 |
| 2217261 | 3/1973 | Fed. Rep. of Germany | 623/38 |
| 2711551 | 9/1978 | Fed. Rep. of Germany | 623/27 |
| 1477401 | 5/1989 | U.S.S.R. | 623/55 |
| 978586 | of 0000 | United Kingdom . | |
| 2127698 | 4/1984 | United Kingdom | 623/38 |

OTHER PUBLICATIONS

Atlas of Limb Prosthetics: Surgical and Prosthetic Principles, AAOS, Mosby: St. Louis (1981), pp. 59-62.
Burgess et al., "Development and Preliminary Evaluation of the VA Seattle Foot", Journal of Rehabilitation Research and Development, 22 (3) 75-84, 1985.

*Primary Examiner*—Randall L. Green
*Assistant Examiner*—D. Willse
*Attorney, Agent, or Firm*—Oblon, Spivak, McClelland, Maier & Neustadt

[57] ABSTRACT

A lower limb prosthesis as a prosthetic foot and an elongate rod formed substantially of unidirectional long fibers embedded in a thermoplastic matrix, the fibers extending substantially parallel to the length of the rod. An adjustment apparatus for the prosthesis includes a pair of pods which may be clamped to the rod and rotated at controlled angles once the thermoplastic rod has been heated to its deformation temperature.

17 Claims, 7 Drawing Sheets

ADJUSTABLE LOWER LIMB PROSTHESIS AND APPARATUS AND METHOD FOR THE ADJUSTMENT THEREOF

BACKGROUND OF THE INVENTION

1. Field of the Invention

The present invention is directed to lower limb prosthesis. More particularly, the present invention is directed to the adjustment of lower limb prosthesis to suit the ambulatory characteristics of the amputee to which it is to be fitted.

2. Background of the Related Art

Lower limb prosthetic devices are presently comprised of two basic classifications. One classification, termed exoskeletal prosthetic devices, relates to devices where the vast majority of the vertical load of the amputee is supported by the shell of the prosthetic appliance. This shell has basically the same exterior shape of the lost limb, and is usually manufactured from a combination of wood and rigid thermoset plastics reinforced with some type of long fiber, to which a separate plastic foot may be attached. This construction renders the prosthesis hard to the touch, but it may be coated with a thin layer of flexible material for cosmetic reasons.

The second type of lower limb prosthetic appliance is termed endoskeletal. This classification relates to a device which carries the vast majority of the vertical load through an inner supporting member. This inner member, or framework, has a shape totally unrelated to that of the missing limb. This inner structure is subsequently covered with a light weight flexible foam, which is then given the proper shape. This structure may or may not include an attached prosthetic foot. If a prosthetic foot is not included in the basic design, a separate prosthetic foot is attached.

An AK (above knee) prosthetic appliance most always includes a knee joint, which is the axis about which the shin portion of the prosthesis rotates. A BK (below knee) prosthesis would usually not contain this knee joint, and would be used in cases in which the length of the residual limb is sufficient to support a prosthetic appliance.

A below knee (BK) endoskeletal prosthesis can further be divided into two smaller classifications. As of this date, they are not specifically named, but can be described as follows. The more popular prosthetic device, which is accepted as the worldwide standard, is comprised of separate foot and shin members, which may be fabricated from components of different manufacturers due to modular design features that exist in much of the componentry available today. This appliance consists of a rigid rod or tube made of metal or thermoset composite material (with the reinforcing fiber always being glass or carbon) attached to a custom fabricated cup or socket which contains the residual limb. At the other or lower end of this rigid structural tube is the prosthetic foot.

Walking is a complex movement which involves not only the pivoting of the lower limb around the knee joint, but also a rotation of the lower limb about its length. It is also necessary to obtain an optimal position of the foot relation to the prosthetic socket using the "trial and error" approach. For this reason, lower limbs are not perfectly straight but are slightly bent and twisted by amounts unique to a given individual. It is therefore common practice to provide lower limb prostheses with angular adjustments tailored to the comfort and gait of the individual wearer. For this purpose, before receiving a permanent prosthesis the amputee is given a "temporary leg." This is a somewhat cumbersome device containing many adjustable features to help determine the proper alignment for the amputee. After a sufficient amount of time walking on the temporary leg, the prosthetist is able to determine the proper relationship between the prosthetic foot and the socket of the residual limb. This temporary leg is then placed in an apparatus called a bench mounted alignment fixture, a device common to the industry. The socket, which can be reused, is positioned and held firmly by this device and the position of the foot relative to this socket is then noted and recorded. The temporary leg, with the exception of the socket, is removed from the bench mounted alignment fixture, making the socket ready for the installation of a permanent prosthesis.

The conventional permanent prostheses all use angularly adjustable adaptors at the ends of a rigid rod. An example may be found in British patent specification No. 978,586 which uses a pair of lockable ball joints at the ends of a tube and connecting the tube to both the prosthetic foot and the socket. Although such adaptors (e.g., ball joints) give the prosthesis the advantage of adjustability, they have two pronounced disadvantages. They add weight and allow the possibility of failure due to the mechanical fasteners they contain becoming loosened during normal usage.

Additionally, in order to allow limited rotation about an axis parallel to the length of the tube, a separate device for rotation should be added. However, such a rotator, although it is highly desirable since it reduces the frictional forces generated between the residual limb and the socket, is seldom used because of the resulting additional weight. Additional weight increases the swinging mass of the leg and requires additional force to maintain the prosthesis firmly attached to the residual limb. Such additional force almost always irritates scar tissue in the area of the amputation and/or further restricts the flow of blood to the most critical areas.

An additional shortcoming of conventional lower leg prostheses is the undesirable transmission of vibrations from the foot, through the tube or rod of the prosthesis, and to the residual limb.

The second or hybrid classification of existing BK prosthesis is that shown in U.S. Pat. No. 4,865,612, which contains a shank and foot constructed of one continuous member. In this case, the supporting inner member is not a tube but is of a solid, flat rectangular cross section, the wider portion running side to side. This single member design continues with a smooth radius in the area of the ankle and out to the toes. The material from which it is manufactured is basically a combination of carbon and fiberglass fibers, the majority of which run in the direction from prosthesis socket to prosthetic toe, contained in a thermoset epoxy matrix. This renders the prosthesis relatively rigid, but does allow bending under load. This bending under load takes full advantage of the composite materials by storing the energy input to the system due to the bending forces, and returning it at a later point in the gait of the amputee. Such energy storage and release is advantageous to more active amputees such as joggers and other sports enthusiasts, but is of little assistance and possibly even detrimental to the majority of amputees. The ability of this construction to allow sufficient rotation about the vertical axis is also extremely limited. This is primarily due to the cross section area being rectangular in shape, the dimensions of this cross section, the orientation of fiber directions, and the rigid thermoset matrix that bonds the fibers together. Alignment changes are also extremely difficult and expensive. Moreover, an added attribute is the composite's high strength to weight ratio, resulting in a relatively lightweight prosthesis. The importance to the amputee of this weight reduction over conventional prosthetic appliance construction cannot be underestimated.

SUMMARY OF THE INVENTION

It is an object of the present invention to provide a prosthetic lower limb and method and apparatus for adjusting the same which allows adjustment at any point in the useful life of the limb without major modifications.

It is a further object of the present invention to provide a lower limb prosthesis which is notably lighter in weight than conventional prostheses.

It is a further object of the present invention to provide a lower limb prosthesis providing limited rotation about an axis parallel to the rod thereof, thereby reducing torque forces between the socket and the residual limb.

It is a further object of the present invention to provide a lower limb prosthesis which minimizes the number of fasteners which can become loose.

It is yet a further object of the present invention to provide an apparatus for adjusting a lower limb prosthesis which is formed of components which can be readily replaced if necessary.

The above, and other, objects are achieved according to the present invention by a lower limb prosthesis comprising a prosthetic foot and an elongate rod having one end fixed to the foot and a proximal end, the elongate rod being formed substantially of unidirectional long fibers embedded in a thermoplastic matrix, the fibers extending substantially parallel to the length of the rod.

According to a further feature of the invention, a lower leg prosthesis adjustment apparatus for the lower limb prosthesis includes means for heating the rod to a temperature such that the matrix is thermoplastically deformable and means for deforming the rod about at least one axis, whereby the rod may be heated and bent for adjustment of the prosthesis.

According to a further feature of the invention, a method for adjusting the lower limb prosthesis includes the steps of heating the rod to a temperature such that the matrix is thermoplastically deformable, deforming the heated rod about one axis, and permitting the deformed rod to cool.

According to a further feature of the invention, there is provided a gripping pod for use with the lower leg prosthesis adjustment apparatus for adjusting the lower limb prosthesis, the gripping pod including a body defining an axis and having a semi-spherical surface centered on the axis, an axial extension of the body having external cam surfaces, and an axial bore extending through the body and the extension.

Since the invention provides adjustability for the lower limb prosthesis by heating the support rod formed with a thermoplastic resin to a temperature at which the thermoplastic resin softens, and providing adjustment by bending the support rod, there is no need for a permanent adjustment mechanism which can become loosened and which adds weight to the prosthesis. Additionally, the support rod having a thermoplastic resin is able to damp vibrations from reaching the socket. Additionally, the support rod has unidirectional long fibers extending substantially parallel to the length of the rod. This permits the support rod to act as a torsional spring and provide limited and controlled rotation of the prosthetic foot relative to the socket during ambulation of the wearer.

DETAILED DESCRIPTION OF THE PREFERRED EMBODIMENT

Figure 1:
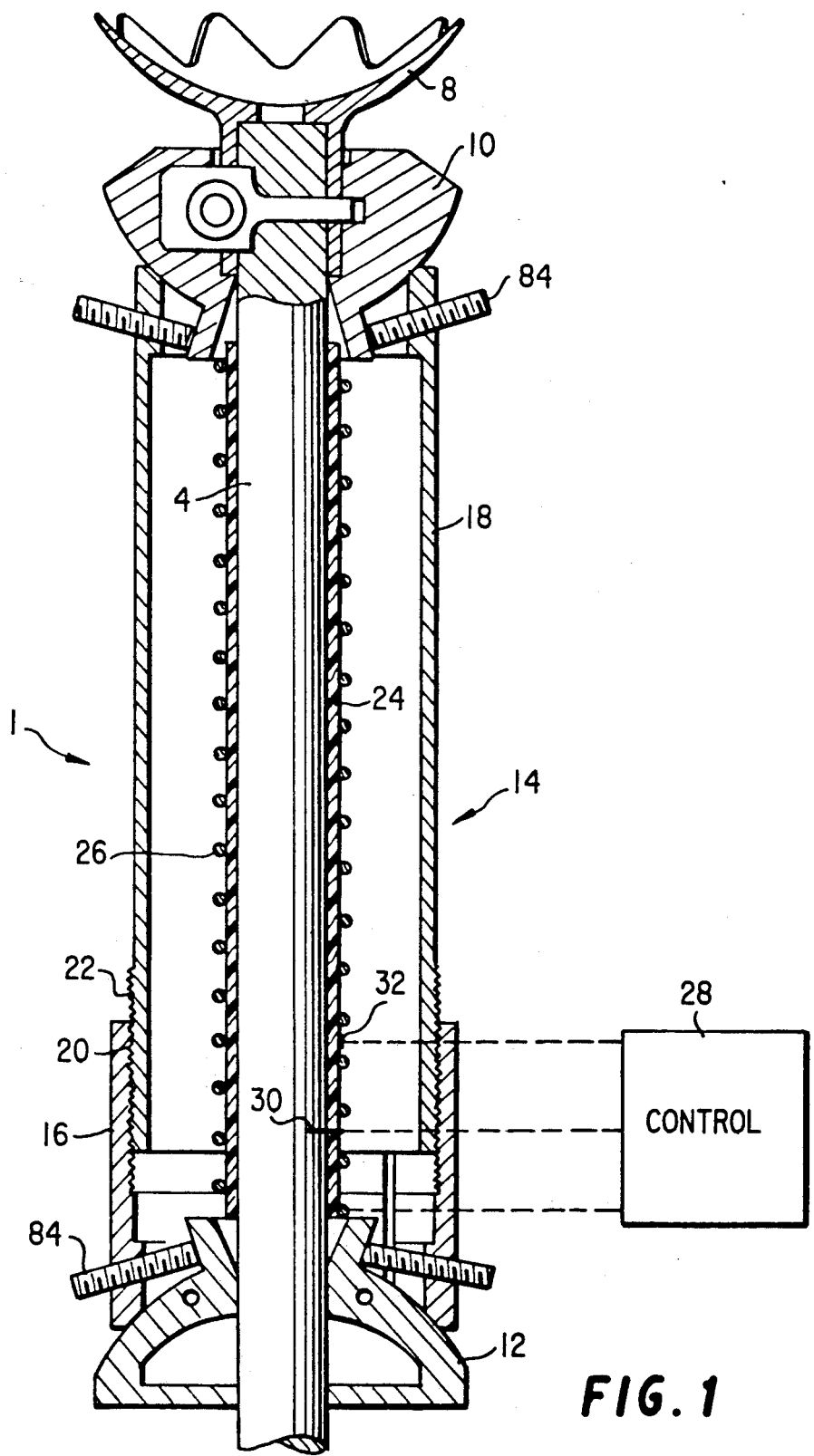
FIG. 1 is a sectional view of an embodiment of the assembled lower leg prosthesis adjustment apparatus.

In the following, non-limiting, example, the same reference numerals will be used to reference the same or corresponding parts throughout the several views.

Figure 7:
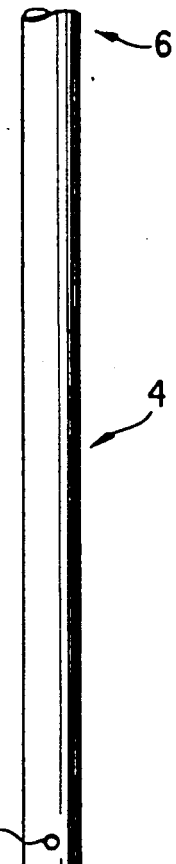
FIG. 7 shows the BK prosthesis prior to application of the prosthesis adjustment apparatus.
Figure 7:
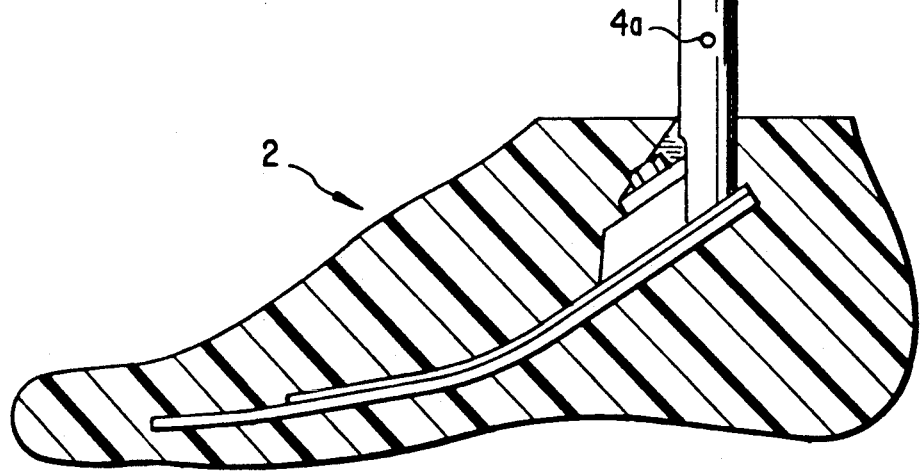

Referring to FIG. 7, a BK endoskeletal prosthesis according to the present invention is shown. It comprises two main elements, a foot prosthesis 2 and a lower limb prosthesis 4. The foot prosthesis 2 can be that according to U.S. Pat. No. 4,865,612. For a detailed illustration of the preferred foot prosthesis, reference can be had to that patent. The lower limb prosthesis 4 comprises a solid straight rod having a lower end fixed to the foot prosthesis 2, and having an opposite proximal end 6. The diameter of the rod 4 is selected by the prosthetist who is to assemble the prosthesis. This diameter will be selected from 2 to 4 standard sizes. A larger diameter is required for heavier amputees and also for those amputees who may demonstrate a very active lifestyle. A smaller diameter would be applicable to light weight amputees or amputees exhibiting a limited activity level. The rod 4 is constructed of unidirectional fibers embedded in a thermoplastic matrix. The predominant direction of the fiber placement is as near parallel with the axis of the rod as is possible. This configuration permits resistance to vertical loads applied by the amputee in normal usage, while absorbing limited torsional stresses about the longitudinal axis of the rod, to thereby absorb torsional loads arising during walking, i.e., limited rotation of the socket relative to the prosthetic foot is possible during ambulation. This significantly reduces abrasion to the skin on the residual limb of the amputee. Further, the ability of the thermoplastic of which the matrix is composed to absorb shocks and dampen vibrations transmitted from the foot to the socket is realized.

The preferred thermoplastic matrix of the fiber/matrix system is nylon 6, due to its high impact resistance, low melting point, and relatively high tensile strength and fatigue resistance. Other matrices such as nylon 6/6, nylon 12, glycol modified polyethylene terapethalate (PET-G), and low molecular weight nylon 6 could also be used effectively. The preferred fiber reinforcing material is carbon or graphite fibers due to their stiffness, their high strength to weight ratio, and their high coefficient of thermal conductivity. Fiberglass reinforcing fibers, polyethylene based Spectra fibers (Allied Chemical), Kevlar 49 or 149 (Dupont) and others may be substituted. The tensile modulus (17,000,000 to 30,000,000 psi) and high ultimate strength (up to 700,000 psi) of the carbon fibers, coupled with the unidirectional configuration, permit the completed prosthesis to adequately resist vertical loads with only minimal resistance to torsion.

As earlier discussed, the rod 4 is constructed principally of carbon unidirectional fibers in a nylon matrix. In this construction, it is imperative that the carbon fibers remain as long as possible and as straight as possible. This dictates that either compression or pultrusion molding techniques of continuous or near continuous fibers be utilized. Since the distal end of the rod 4 requires a particular shape other than that of the normal cross section, this requires either compression molding be employed (the preferred method) or pultrusion and subsequent post-forming of the distal end of the rod (alternative method). Conventional injection molding is inadequate in that extremely short fiber lengths (approximately ⅛ to ½ inches) result. This drastically reduces the mechanical properties along the axis of the rod, which necessitates an increase in the diameter and thereby increases the torsional resistance due to the composite becoming more isotropic, resulting in an increase in the frictional forces at the socket/residual limb interface.

Figure 6:
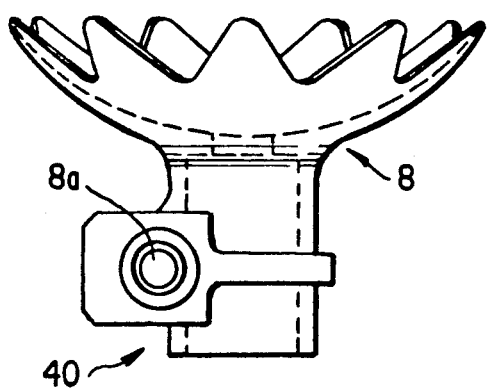
FIG. 6 is a side elevation view of the socket adaptor in the apparatus of FIG. 1.

The proximal end 6 of the prosthesis is attached to a conventional socket (not shown) via an adaptor 8 (FIG. 6) which is fixed to the proximal end 6 of the prosthesis. However, before the prosthesis can be properly worn, it is necessary to adjust the prosthesis to the gait of the wearer by adjusting the angular relationship between the prosthetic foot 2 and the socket of the residual limb, using adjustment criteria determined by the prosthetist based upon adjustments made to the temporary leg.

According to the present invention, rather than providing adaptors for adjusting the prosthesis, the rod 4 is bent about axes transverse to its length, at two positions along its length. This is done by adjustment of the apparatus 1 shown in FIGS. 1–5 and 8.

Referring to FIG. 1, the adjustment apparatus 1 has the following main components: An upper pod 10 is clamped to the proximal end of the rod 4 at a position surrounding the lower portion 40 of the adaptor 8. A lower pod 12 is clamped to the lower end of the rod 4. Between the pods 10 and 12 extends an adjustable cylinder 14, whose length is adjustable in the axial direction. The cylinder 14 is in fact composed of a lower cylinder element 16 and an upper cylinder element 18. The lower and upper cylinder elements are connected to one another in an axially adjustable manner, for example by meshing threads 20 and 22 at the joined ends of the cylinder elements.

A silicone sleeve or cover 24 surrounds the portion of the rod between the pods 10 and 12, and at least a part of the length of the silicone cover is in turn covered by a heating means, such as a flexible resistance heating coil 26 wound around the sleeve 24. The coil 26 heats the rod 4 when it is energized by electrical current via the control unit 28. The control unit 28 receives temperature signals from a core temperature sensor 30 and a surface temperature sensor 32.

Figure 2A:
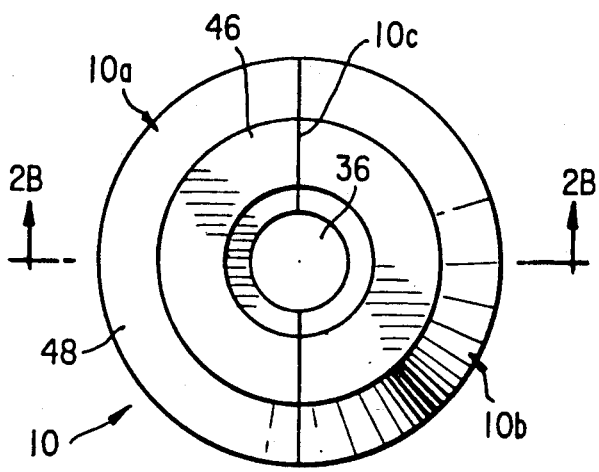
FIG. 2A is a top view of an upper pod of the apparatus of FIG. 1.
Figure 2B:
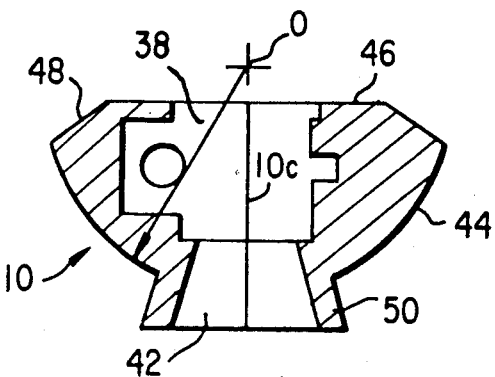
FIG. 2B is a sectional view along line 2B—2B in FIG. 2A.
Figure 2C:
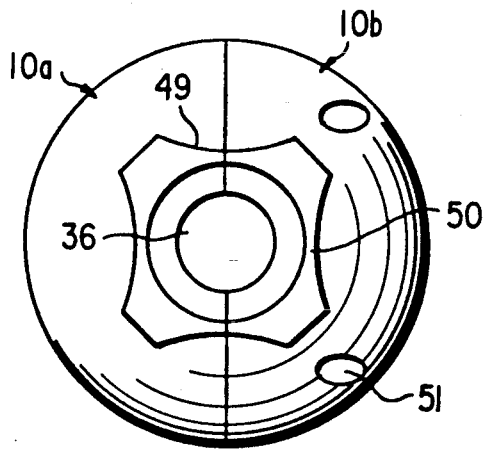
FIG. 2C is a bottom view of the pod of FIG. 2A.

Referring to FIGS. 2A through 2C, the upper pod 10 is formed of two substantially symmetrical halves 10a and 10b which are divided along a median plane 10c. The pod is formed of metal or rigid plastic, preferably of aluminum, as are the pod 12 and the cylinder elements 16 and 18. It defines a central bore 36 which is bisected by the plane 10c. The central bore 36 has a main portion which is shaped to accommodate the lower portion 40 of the adaptor 8, and a lower portion 42 which is tapered outwardly in a direction from the main portion towards the bottom of the bore.

The peripheral surface of the main body of the upper pod 10 takes the form of a semi-spherical surface 44 truncated by a planar top surface 46 which may have a bevel 48 at its boundary with the semi-spherical surface 44. The semi-spherical surface 44 is centered at point O which lies on the plane 10c and substantially coincides with one of the axes of bending of the rod 4, as will be explained later. An annular skirt 50 depends from the lower part of the semi-spherical surface 44 and forms a unitary extension of the upper pod. This skirt 50 surrounds and defines the lower portion 42 of the bore.

The skirt 50 exteriorly defines a plurality of cam surfaces 49; 4 in the preferred embodiment. Each of these cam surfaces 49 is slightly convex and tapers outwardly towards its distal end. In the preferred embodiment, adjacent cam surfaces are angularly separated by approximately 90°. It may be appreciated that more or fewer than 4 such cam surfaces may be provided.

The two halves 10a and 10b of the upper pod 10 may be placed around the proximal end of the rod 4 and clamped firmly thereon by bolts which extend through apertures 51 of the pod half 10b and which are threaded into aligned threaded holes (not shown) of the pod half 10a. Pods having bores 36 of diameters corresponding to the diameters of the selected rods 4 may be used.

Figure 3A:
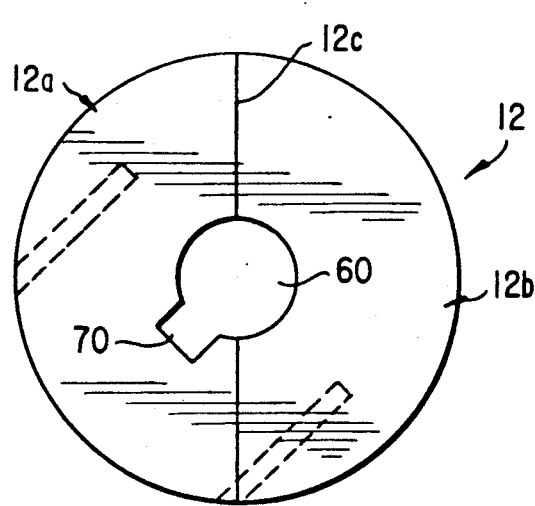
FIG. 3A is bottom view of the lower pod of the apparatus of FIG. 1.
Figure 3B:
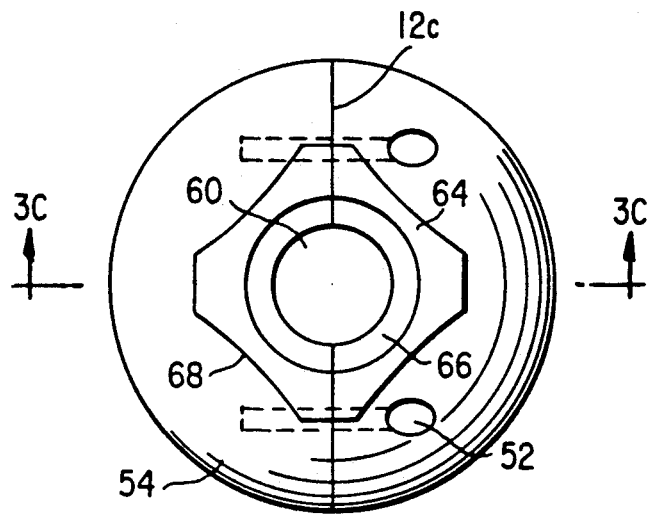
FIG. 3B is a top view of the pod of FIG. 3A.
Figure 3C:
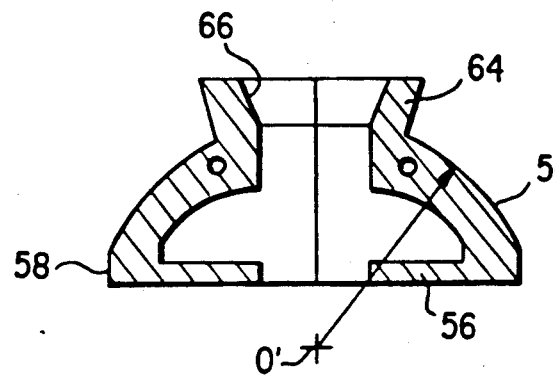
FIG. 3C is a sectional view taken along line 3C—3C in FIG. 3B.

The lower pod 12 shown in FIGS. 3A through 3C is similar to the upper pod 10. It is also composed of two symmetrical halves 12a and 12b which may be clamped together by bolts (not shown) inserted in holes 52 of one of the pod halves. It also has a semi-spherical peripheral surface 54 centered on point O'. The spherical surface is truncated by a planar bottom surface 56, optionally through the intermediary of a short cylindrical surface 58. A bore 60 extends through the lower pod and is bisected by the separating plane 12c of the two pod halves. A depending skirt 64 defines the outwardly tapered upper portion 66 of the bore 60. The outer periphery of the skirt 64 defines, in the illustrated embodiment, 4 convex cam surfaces 68. The key hole 70 engages an optional key or some other aligning element at the base of the rod 4 for setting the rotational position of the lower pod 12.

Figure 4A:
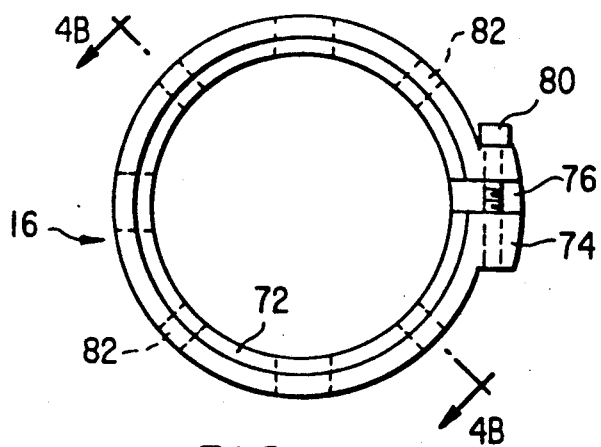
FIG. 4A is a top plan view of the lower cylinder element in the apparatus of FIG. 1.
Figure 4B:
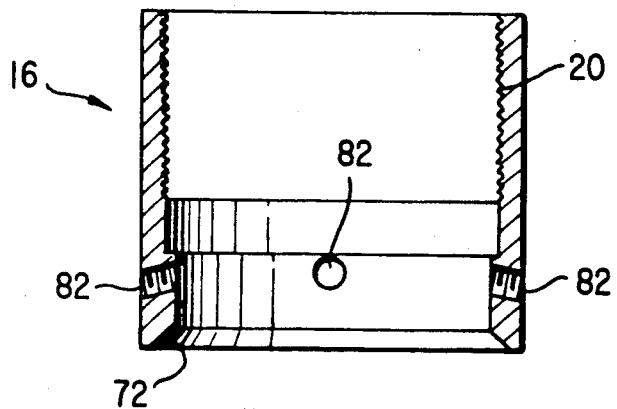
FIG. 4B is a section taken along line 4B—4B in FIG. 4A.
Figure 4C:
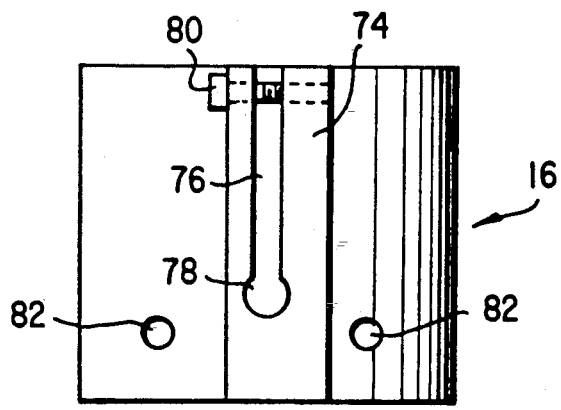
FIG. 4C is a front elevation view of the cylinder element of FIG. 4A.

Referring to FIGS. 4A through 4C, the lower cylinder element 16 has a bevelled lower inner edge 72 which is intended to bear against the semi-spherical surface 54 of the lower pod 12. A portion of the periphery of the lower cylinder is thickened to form an axially extending flange 74, through which is partially cut a gap 76 having a widened base 78. A bolt 80 clamps the portions of the flange 74 on opposite sides of the gap 76, near the top thereof, in order to clamp onto the upper cylinder element, as will be described below.

Four equally spaced threaded holes 82 are formed in an optionally thickened lower portion of the lower cylinder element 16. These holes 82 extend substantially radially but preferably do not extend transverse to the axis of the cylinder. They are instead slightly angled from a plane transverse to the cylinder axis by the same angle as the outward tapering of the skirt 64, for example by 16 degrees. Adjusting elements 84 (FIG. 1) in the form of threaded rods are threaded into each of the holes 82 until they abut one of the cam surfaces 68.

Figure 5A:
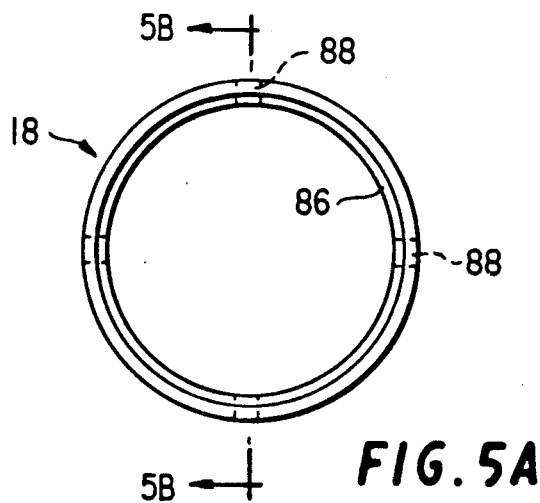
FIG. 5A is a top plan view of an upper cylinder element in the apparatus of FIG. 1.
Figure 5B:
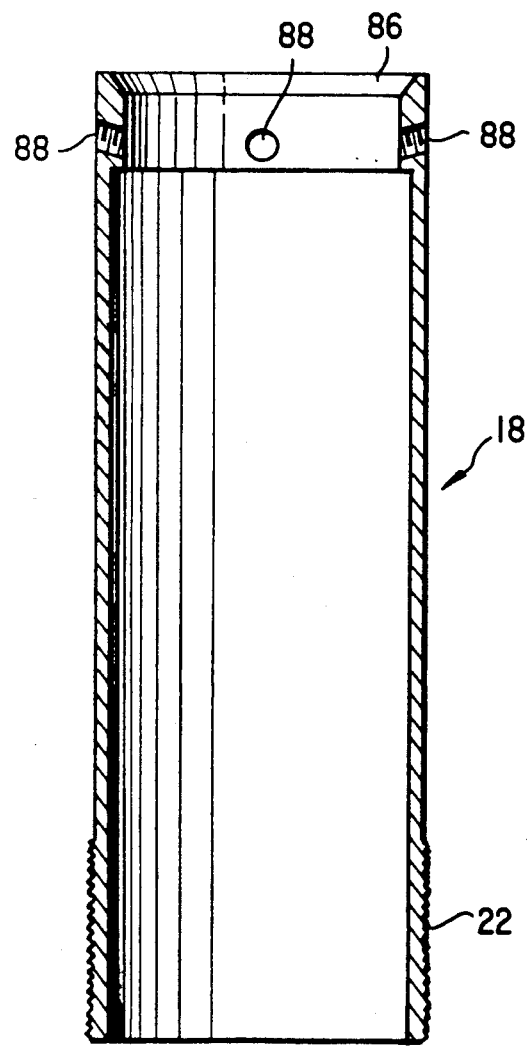
FIG. 5B is a sectional view taken along line 5B—5B in FIG. 5A.

Referring to FIGS. 5A and 5B, the upper cylinder element is substantially identical to the lower cylinder element, except that it has the screw threads 22 on the outer periphery thereof and lacks the flange and gap. It has an annular bevel 86 in its top end, and also has threaded holes 88 for adjusting elements 84. The threaded holes 88 extend radially and are angled with respect to a plane transverse to the cylinder axis by an angle which preferably equals the taper angle of the skirt 50, e.g., 16 degrees.

The elements are assembled in preparation for an adjusting operation, as follows:

First, the silicone sleeve 24 is placed around the rod 4. The silicone sleeve is intended to help maintain the shape of the soft thermoplastic of the rod 4 when it is heated. The interior cross section of the silicone sleeve 24 should be slightly smaller than the exterior cross section of the rod 4, so that the silicone sleeve compresses the rod. The silicone sleeve may be fiber reinforced for increased strength and/or to help produce the desired shape.

Prior to assembly, a bore hole 4a has been bored into the rod 4 by a distance sufficient so that the core sensor 30 can be inserted therein and sense the core temperature of the rod 4. The sleeve 24 is positioned over the core sensor 30. To do this a hole is bored in the sleeve and the core sensor is inserted into the bore hole 4a through the hole in the sleeve. The surface temperature sensor 32 is mounted on the sleeve itself. Each of the temperature sensors 30 and 32 can be a thermocouple sensor of a conventional type.

Subsequently, the heater coil 26 is wound around the sleeve 24 and the lower pod 12 is clamped onto the lower portion of the rod 4 to tightly grip the rod 4, the lower cylinder element 16 is laid on the lower pod 12, and upper cylinder element 18 of a desired length is selected and threaded into the lower cylinder element. The lead wires of the heating coil and the temperature sensors are extended through the gap 76 prior to attachment of the upper cylinder element. The adaptor 8 is lightly clamped onto the proximal end of the rod 4 by the adaptor bolt 8a, and the upper pod 10 is clamped onto the distal end of the rod 4 over the lower portion 40 of the adaptor 8. The upper cylinder element is then rotated until the bevelled ends of the cylinder elements 16 and 18 tightly abut the semi-spherical surfaces of the pods. At this time, the bolt 80 is tightened so as to lock the axial length of the cylinder 14. The adjusting elements 84 are then adjusted to abut the cam surfaces, so that the positions of the pods 10 and 12 are stabilized. It should be noted that the adaptor 8 only lightly grips the rod 4 and can slide thereon. The upper pod 10 is clamped on the adaptor 8 and so also only lightly grip the rod 4, which permits necessary sliding of the upper pod on the rod during an adjustment procedure.

For the adjustment operation, heater is turned on, whereby the controller 28 causes a current of approximately 3–4 amps to flow through the flexible coil 26 for a set time such as approximately six minutes (or a shorter time, as described below). This is the optimal time with the smallest (18 mm) diameter rod. Heating time will increase as larger diameter rods are utilized. During heating of the rod, two criteria must be controlled. Heating must be sufficient for the core of the rod to reach a softening temperature, typically approximately 420° F. However, the outer surface of the rod must be maintained below a maximum temperature of about 550° F.; higher temperatures can result in uncontrolled flow of the softened matrix and damage of the silicone sleeve will occur.

Once the rod 4 has reached its softening temperature, it can be thermoplastically deformed by adjustment of the adjusting elements 84. Thus, by adjusting two radially opposed elements 84 on the upper pod 10, one can deform the proximal end of the rod 4 about an axis lying substantially on the center point O and directed transverse to the axis of the rod 4. Adjustment of the other two opposing adjustment elements 84 abutting the upper pod 10 causes deformation of the proximal end of the rod 4 by pivoting about an axis which also lies substantially on the center point O, extends transverse to the longitudinal axis of the rod 4, and is transverse to the earlier mentioned bending axis. Adjustment is performed to set the bending angle to a value determined by adjustment of the temporary leg. A similar procedure is carried out for the lower pod 16.

Once the above procedure is completed and the rod has cooled, the mobile alignment fixture is removed by an assembly sequence opposite to that set forth above.

Figure 8:
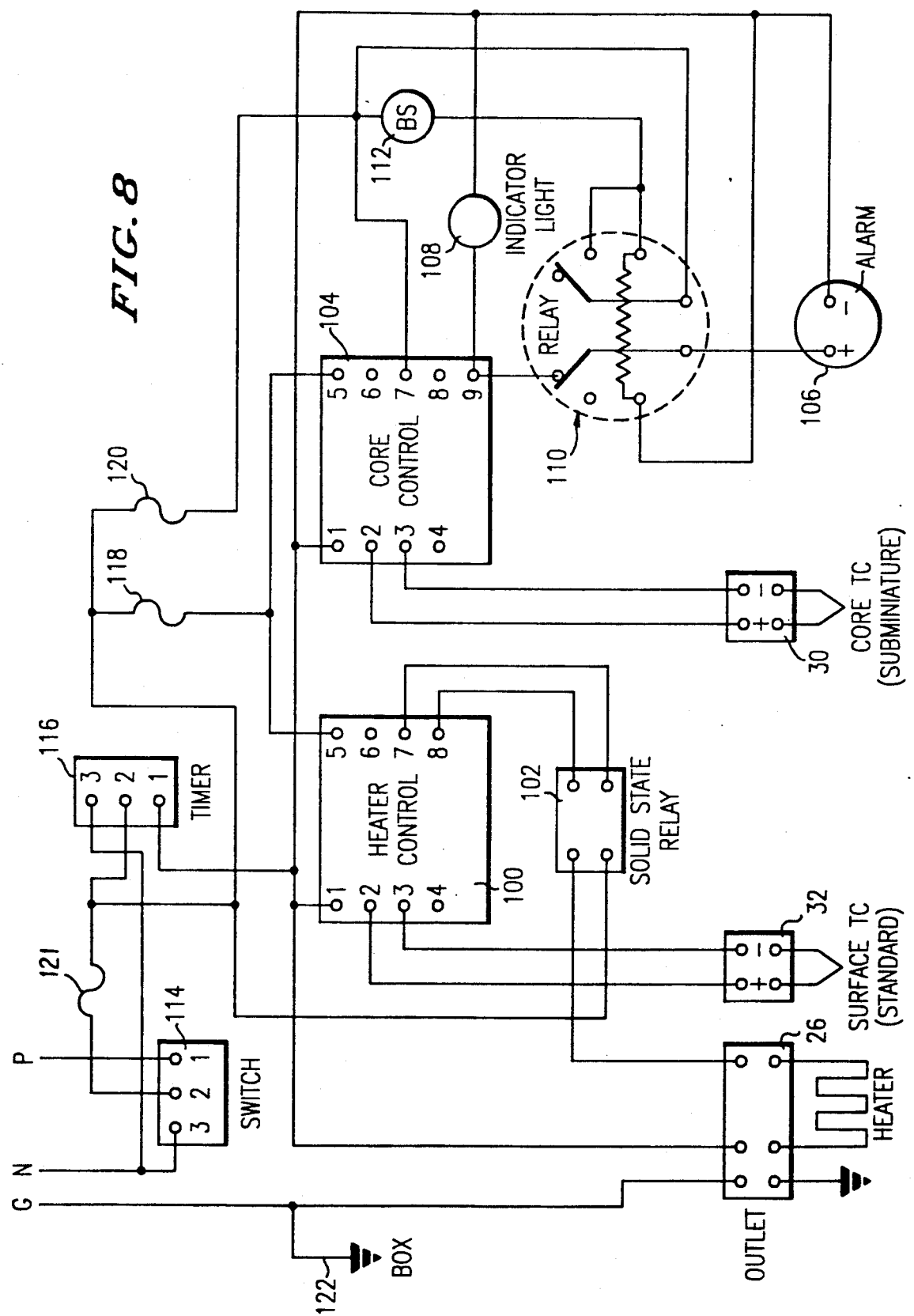
FIG. 8 is a circuit diagram of the heater control system.

Any heater control can be used which is capable of sensing the core and surface temperatures and heating the rod while preventing overheating. A preferred control 28 is schematically shown in FIG. 8. It includes a temperature controller 100, which may be the SHIMADEN Model SR34, which controls the current to the heater 26 via a solid state relay 102, which is preferably the CRYDOM Model D2410. The temperature controller 100 is a set point type controller which thermostatically limits current to the heat element 26 when the surface sensor 32 detects the surface temperature higher than that set for the controller (e.g. 550° F.). The core temperature controller 104 is preferably the SHIMADEN Model SR32, and emits signals to an alarm 106 and an indicator light 108, via a relay 110 when the core temperature sensor 30 senses that the melt point or deflection point temperature of the thermoplastic material has been reached. Current to the alarm can then be shut off via the button switch 112. Although not shown, the core temperature controller 104 should continuously display the core temperature. Optionally, the alarm 110 can be made to notify the user when the temperature has reached a point beyond which the thermoplastic material may begin to degrade, or some other relevant point.

The switch 114 is included to energize the other components, while an interval timer 116 is set to limit the maximum time that the thermoplastic part can be heated during each shaping session, e.g., 45 minutes. This is especially important for materials which tend to degrade when exposed to elevated temperatures for extended periods of time. Also provided are fuses 118, 120 and 121, as well as a ground fault circuit interrupter (not shown). Ground is shown at 122.

If the alignment procedure is not satisfactory, the fixture can be reinstalled in the manner set forth above and the heating cycle repeated.

The total weight of an average BK prosthesis according to the present invention is approximately 15-35% lighter than one manufactured by conventional techniques. This is primarily due to the composite materials used and the elimination of the additional weight resulting from torque absorbers and adaptors. A very significant savings in labor may also be demonstrated. The prosthesis is subsequently completed using conventional endoskeletal techniques of shaping and installing of a soft, flexible foam cover which is placed over the tubing.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A lower leg prosthesis adjustment apparatus for adjusting a lower limb prosthesis including a prosthetic foot and an elongate rod having one end fixed to the foot and a proximal end, the elongate rod being formed substantially of unidirectional long fibers embedded in a thermoplastic matrix and extending substantially parallel to the length of the rod, said apparatus comprising:
   means for heating the rod to a temperature such that the matrix is thermoplastically deformable; and
   means for deforming the rod about at least one axis, whereby the rod may be heated and bent for adjustment of the prosthesis.

2. The apparatus of claim 1, wherein said means for deforming comprise means for deforming the rod about at least two spaced axes perpendicular to the length of the rod.

3. The apparatus of claim 2, wherein said means for deforming the rod comprise:
   means for gripping the rod at two portions on the length of the rod; and
   means for pivoting the gripping means about said axes.

4. The apparatus of claim 3, wherein said gripping means comprise two pods, each of said pods having a portion fittable on the rod for gripping the rod, each said pod having at least one cam surface spaced from the gripping portion in the direction of the length of the rod when the pod is fitted on the rod.

5. The apparatus of claim 4, wherein said pivoting means comprise:
   a frame mountable on the prosthesis and between said pods so as to be stationary relative to the rod; and
   adjustment elements mounted on said frame and engagable with said at least one cam surface of each said pod for pivoting said at least one cam surface, whereby adjustment of said adjustment elements pivots said pods about said axes perpendicular to the length of the rod.

6. The apparatus of claim 5, wherein said frame comprises a cylinder, wherein said pods each have semispherical surface fitted in an end of said cylinder, so that said pods each pivot about the center of said semispherical surface and wherein said cylinder is mountable on the prosthesis via said pods being fitted on the rod.

7. The apparatus of claim 6, wherein said adjustment elements comprise screws threaded in said cylinder and abutting said cam surfaces.

8. The apparatus of claim 6, wherein said cylinder comprises two cylinder elements axially adjustably fitted to one another, whereby said spherical surfaces of said pods may be tightly abutted to the ends of said cylinder.

9. The apparatus of claim 6, including a socket adapter fittable in one of said pods, and means on said socket adaptor for fixing said socket adaptor to the rod.

10. The apparatus of claim 1, wherein said heating means comprise a thermostatically controlled electrical heating coil wound around the rod.

11. The apparatus of claim 10, including a high temperature silicone sleeve fittable between the rod and said heating coil.

12. The apparatus of claim 10, wherein said heating means include a controller sensitive to a core temperature of the rod and a surface temperature of the rod, said controller including means for thermostatically limiting a maximum surface temperature of the rod.

13. A method for adjusting a lower limb prosthesis including a prosthetic foot and an elongate rod having one end fixed to the foot and a proximal end, the elongate rod being formed substantially of unidirectional long fibers embedded in a thermoplastic matrix and extending substantially parallel to the length of the rod, comprising the steps of:
   heating the rod to a temperature such that the matrix is thermoplastically deformable;
   deforming the heated rod about at least one axis; and
   permitting the deformed rod to cool.

14. The method of claim 13, wherein said deforming step comprises:
   positioning around said rod a cylinder having gripping pods abutting opposite ends of the cylinder, the pods gripping the ends of the rod, and
   pivoting at least one of the pods to a desired adjustment angle relative to the cylinder.

15. The method of claim 14, wherein said heating step comprises fitting a heating coil around the rod prior to said step of positioning the cylinder around the rod; and activating the heating coil.

16. The method of claim 15, wherein said positioning step comprises adjusting the length of the cylinder such that pods tightly abut the ends of the cylinder.

17. The method of claim 15, wherein said pivoting step comprises adjusting adjustment elements fitted in the cylinder and abutting a cam portion of one of said pods.

* * * * *